United States Patent [19]

Iguchi et al.

[11] Patent Number: 5,756,553
[45] Date of Patent: May 26, 1998

[54] MEDICAL MATERIAL AND PROCESS FOR PRODUCING THE SAME

[75] Inventors: Seiichiro Iguchi; Rika Higashino, both of Tokushima, Japan

[73] Assignees: Otsuka Pharmaceutical Factory, Inc., Tokushima; Otsuka Pahrmaceutical Co., Ltd., Tokyo, both of Japan

[21] Appl. No.: 403,828

[22] PCT Filed: Jul. 13, 1995

[86] PCT No.: PCT/JP94/01162

§ 371 Date: Mar. 21, 1995

§ 102(e) Date: Mar. 21, 1995

[87] PCT Pub. No.: WO95/03075

PCT Pub. Date: Feb. 2, 1995

[30] Foreign Application Priority Data

Jul. 21, 1993 [JP] Japan ................... 5-180300

[51] Int. Cl.⁶ ................... A61K 47/30; A61F 2/06
[52] U.S. Cl. ................... 514/772.3; 424/425
[58] Field of Search ................... 424/484, 425; 514/772.3; 623/1; 128/768; 604/128

[56] References Cited

U.S. PATENT DOCUMENTS 4,999,210  3/1991  Solomon et al. ................... 424/78
5,013,306  5/1991  Solomon et al. ................... 604/265
5,165,952  11/1992  Solomon et al. ................... 424/78.08
5,328,698  7/1994  Onwumere et al. ................... 424/486

FOREIGN PATENT DOCUMENTS 54-135494    10/1979   Japan .
62-217970     9/1987   Japan .
2-234767      9/1990   Japan .
WO 93/07217   4/1993   WIPO .

OTHER PUBLICATIONS

Levy et al., *Chemical Abstracts*, vol. 121, #263625.

Kambayashi et al., *Chemical Abstracts*, vol. 122, #222732.

Bamford et al., *Chemical Abstracts*, vol. 107, #83769.

*Primary Examiner*—Carlos A. Azpuru
*Attorney, Agent, or Firm*—Sughrue, Mion, Zinn, Macpeak & Seas, PLLC

[57] ABSTRACT

A medical material of the present invention comprises a polymer or copolymer of a vinyl derivative having a polar group, said polymer or copolymer containing an antiplatelet agent. Since the antiplatelet agent can be continuously dissolved in the active concentration, the material has high anticoagulant activity and inhibition action of platelet loss due to activation of platelet.

31 Claims, 6 Drawing Sheets

5,756,553

MEDICAL MATERIAL AND PROCESS FOR PRODUCING THE SAME

TECHNICAL FIELD

The present invention relates to a medical material such as a medical device which directly contacts with blood, and a process for producing the same. More particularly, it relates to a medical material which causes no blood coagulation (thrombogenesis) or platelet loss due to activation of platelet even if the material directly contacts with blood, and a process for producing the same.

BACKGROUND ART

In the medical field, thrombogenesis on the surface of polymer materials used for an artificial heart, artificial lung, vascular prosthesis, catheter, etc., which directly contact with blood is a serious problem. Therefore, medical materials having excellent anticoagulant or anti-thrombogenic activity have been required.

As a method for imparting the anti-thrombogenic activity to medical materials, for example, there have hitherto been known a method(1) of forming a composite of heparin and a polymer material, or a method(2) of immobilizing fibrinolytic enzyme to the surface of a polymer material [for example, see Japanese Laid-Open Patent Publication No. 54-68097 (Japanese Patent Publication No. 60-40861), Japanese Laid-Open Patent Publication No. 56-136564 (Japanese Patent Publication No. 59-51304), Japanese Laid-Open Patent Publication No. 57-75655 (Japanese Patent Publication No. 61-6662) and Japanese Laid-Open Patent Publication No. 57-14358 (Japanese Patent Publication No. 63-43107).

However, the above method (1) has a problem that, there are large restrictions on processing and manufacturing because heparin is thermally unstable, and that sustained release for a long period of time can not be expected because the retention amount of heparin in the material is small.

Further, the above method (2) has a problem that, there are extremely large restrictions on manufacturing because the processing is conducted by surface coating and the treatment is complicated and, further, fibrinolysis activity is liable to be deteriorated by heart, and that sustained effect can not be expected because the absolute amount of a fibrinolytic enzyme in the material is small.

Further, safety of a chemical structure, which is used for a ligand or spacer in case of formation of composite or immobilization, to the human body has not been worked out completely, at present.

On the other hand, materials superior in blood compatibility have also been developed so as not to cause thrombogenesis.

For example, in the field of vascular prosthesis, a vascular prosthesis comprising an expanded poly (tetrafluoroethylene) manufactured by Gore Co., U.S.A. is known. However, in these materials, it is indispensable to produce a porous structure by expanding in order to develop the anti-thrombogenic activity, which results in large restrictions on use application and production process.

Further, a medical material of the polyurethane or polyurethane urea having a microdomain structure, however, the material has a problem that the production process is complicated because of its hard thermal molding, which results in large restrictions on manufacturing, and that constant anti-thrombogenic activity can not be easily obtained because the microdomain structure varies largely depending upon the processing method.

Furthermore, a medical material wherein an antiplatelet agent is blended in a polyurethane or polyurethane urea is proposed, however, the material has a problem that the production process is complicated because of its difficult thermal molding, which results in large restrictions on manufacturing.

On the other hand, it is known that a HEMA (2-hydroxyethyl methacrylate)-styrene copolymer having a microdomain structure has anti-thrombogenic activity. However, it is limited to the coating material because of its small mechanical strength and the field of application is limited to a specific one.

It is a main object of the present invention is to provide a medical material which solves the above technical problems and can be easily produced, and which can uniformly contains an antiplatelet agent and enables continuous release of the antiplatelet agent, and a process for producing the same.

DISCLOSURE OF THE INVENTION

In order to solve the above problems, the present inventors have intensively studied about formation of composites of various drugs and polymer materials. As a result, it has been found that it is possible to formulate an antiplatelet agent, particularly cilostazol, dipyridamole or aspirin in a polymer or copolymer of a vinyl derivative having a polar group, and that a release rate of the antiplatelet agent can be optionally controlled depending upon a kind of the above polymer or copolymer, amount or blending method of the antiplatelet agent, blending of at least one of additive to the polymer or copolymer and the like. Thus, the present invention has been accomplished.

That is, the present invention provides a medical material comprising a polymer or copolymer of a vinyl derivative having a polar group, said polymer or copolymer containing an antiplatelet agent.

DETAILED EXPLANATION OF THE INVENTION

Figure 1:
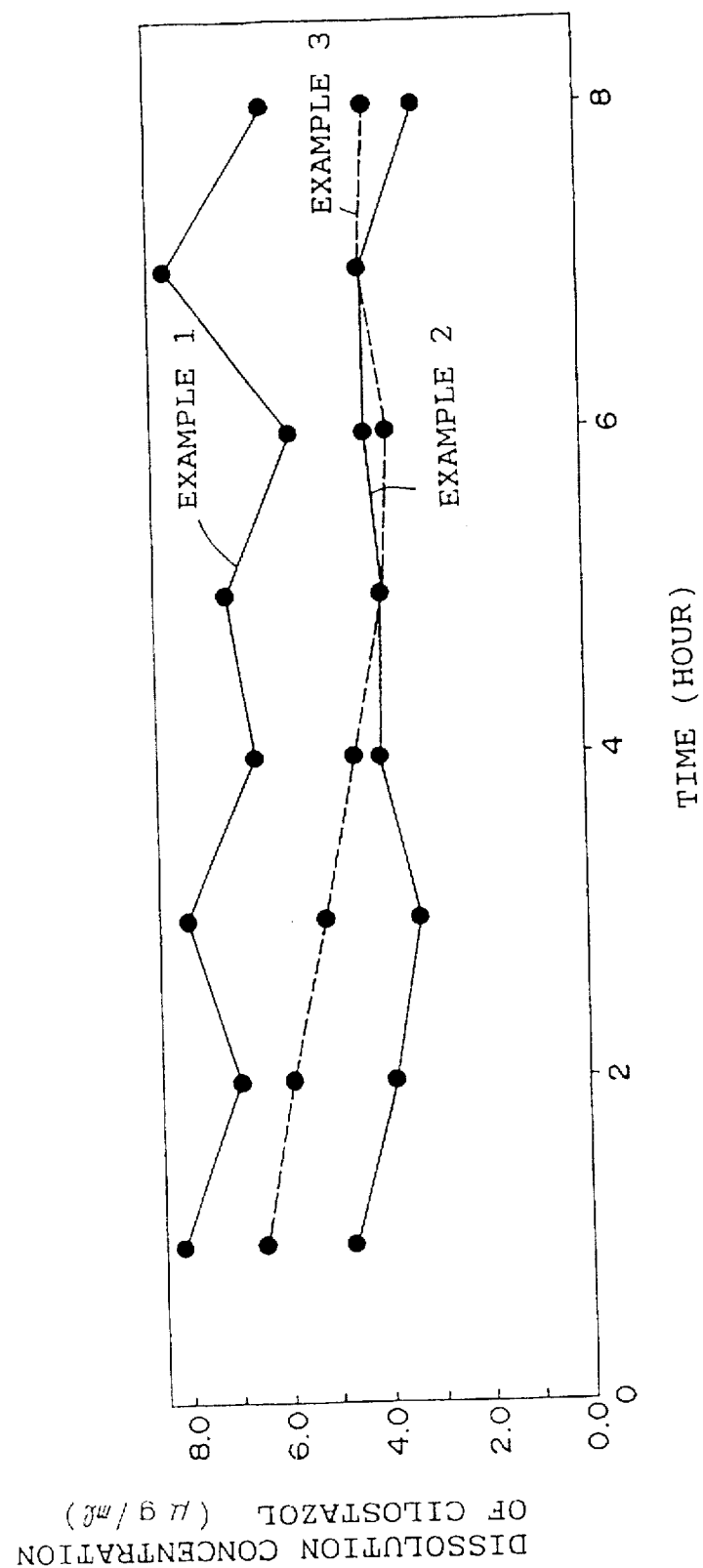
FIG. 1 is a graph illustrating a variation with time in dissolution concentration of drug obtained by using the respective films produced in Examples 1, 2 and 3.

Examples of the polar group include hydroxyl group, chlorine atom, cyano group, alkoxycarbonyl group and the like.

Examples of the polymer or copolymer of the vinyl derivative having the polar group include polyvinyl chloride, polyvinyl alcohol, polyacrylonitrile, polymethacrylate, polyacrylate, vinyl chloride-vinylidene chloride copolymer, ethylene-vinyl alcohol copolymer and the like. In the present invention, it is particularly preferred to use polyvinyl chloride, ethylene-vinyl alcohol copolymer, polymethacrylate, polyacrylate or polyacrylonitrile, more preferably polyvinyl chloride, ethylene-vinyl alcohol copolymer or polymethacrylate. These polymers or copolymers may be used as they are as a main constituent material of the medical material, or they may be used by applying (coating) on or impregnating into the other material. Further, these polymers or copolymers may be used alone, or two or more sorts of them can be combined by mixing or laminating.

The polymer or copolymer used in the present invention has hitherto been used as the material which directly contacts with blood, and it is proved that the polymer or copolymer has extremely high stability and safety. Besides, the polymer or copolymer is stably supplied and is inexpensive.

The polymer or copolymer of the vinyl derivative can be anyone which is suitable as the medical material, and those having various physical properties can be employed. For example, in case of polyvinyl chloride, those having an average degree of polymerization of 800 to 8000, preferably 800 to 4500 are suitable. If necessary, there can be blended plasticizers such as di-2-ethylhexyl phthalate, di-n-decyl phthalate, tri-2-ethylhexyl trimellitate, etc., various stabilizers, secondary plasticizers, lubricants and the like.

On the other hand, in case of the ethylene-vinyl alcohol copolymer, the composition ratio of ethylene to the total amount of the medical material can be appropriately varied according to the usage of the medical material and processing method. Normally, it is preferred that the etylene content is 10 to 80 molar %. When the etylene content exceeds 80 molar %, blood compatibility and dispersibility of the antiplatelet agent becomes inferior. On the other hand, when the amount is smaller than 10 molar %, mechanical strength, water resistance and processing characteristics in a melting method described hereinafter are deteriorated. On the other hand, in case of polymethacrylate, poly(methyl methacrylate) can be suitably used, and those having a low melting temperature are particularly preferred because processing due to the melting method can be easily conducted.

Examples of the antiplatelet agent include cilostazol, dipyridamole, aspirin, ticlopidine, beraprost, indomethacin, sulfinpyrazone, satigrel, d-indobufen, dazoxiben, furegrelate, ozagrel, pirmagrel, dazmegrel, midazogrel, daltroban, sulotroban, vapiprost, clopidgrel, prostaglandin $E_1$, iloprost, limaprost and the like. In addition to the above, there are 2-[4,5-bis(4-methoxyphenyl) thiazol-2-yl]pyrrole-1-acetic acid ethyl ester, 2-methyl-3-(1,4,5,6-tetrahydronicotinoyl)pyrazolo[1,5-a]pyridine, 1-(cyclohexylmethyl)-4-[4-(2,3-dihydro-2-oxo-1H-imidazo [4,5-b]quinoline-7-yloxy)-1-oxobutyl]piperazine, 3-methyl-2-(3-pyridinyl)-1H-indol-octanoic acid, (E)-7-phenyl-7-(3-pyridyl)-6-heptenoic acid, (±)-6-(1-imidazolylmethyl)-5,6, 7,8-tetrahydronaphthalene-2-carboxylic acid, 4-[α-hydroxy-5-(1-imidazolyl)-2-methylbenzyl]-3, 5-dimethylbenzoic acid, 1-(2-carboxyethyl)-2-methyl-3-(1 H-imidazol-1-ylmethyl) indole, (E)-1-[3-(phenylmethoxy)-1-octenyl]-1H-imidazole, 7-[2α,4 α-(dimethylmethano)-6β-(2-cyclopentyl-2β-hydroxyacetamido)-1α-cyclohexyl]5(Z)-heptanoic acid, (E)-11-[2-(5,6-dimethyl-1-benzimidazolyl) ethylidene]-6,11-dihydrobenz[b,e]oxepin-2-carboxylic acid, 5-{(1R,6S,7S,8R)-8-hydroxy-7-[(3S)-3-hydroxy-4,4-dimethyl-1,6-nonadiynyl]-cis-3-bicyclo [4,3,0]non-2-ene-3-yl]}-3-oxapentanoic acid, methyl 5-{(1S,5S,6R,7R)-7-hydroxy-6-[(E)-(S)-3-hydroxy-1-octenyl]bicyclo [3,3,0]oct-2-en-3-yl] pentanoate, [1α,2α(Z), 3β,4α]-(±)-7-{3[ (phenylsulfonyl)amino]-bicyclo [2,2,1] hept-2-yl}-5-heptenoic acid, (−)-cis-3-acetoxy-5-[2-(dimethylamino) ethyl]-2,3-dihydro-8-methyl-2-(4-methylphenyl)-1,5-dibenzothiazepine-4-(5H)-one and the like. They can be used alone or in combination thereof. Among them, cilostazol, dipyridamole, beraprost, satigrel and aspirin can be suitably used. Particularly, cilostazol is preferred.

The amount of the antiplatelet agent is 0.01 to 60 parts by weight, preferably 0.1 to 50 parts by weight, more preferably 1 to 44.4 parts by weight, particularly 4.8 to 33.3 parts by weight, based on 100 parts by weight of the medical material comprising the polymer or copolymer of the vinyl derivative, which contains the antiplatelet agent. When the amount of the antiplatelet agent exceeds the above range, molding properties are inferior. If molding could be conducted, physical properties are deteriorated and, therefore, it is not suitable for practical use. On the other hand, when the amount of the antiplatelet agent is smaller than the above range, it becomes difficult to control release of the antiplatelet agent and anticoagulant effect is deteriorated, which results in no addition effect. Further, as described hereinafter, the release amount of the antiplatelet agent can be controlled by varying the amount of the antiplatelet agent within the above range. In general, there is an upper limit to the dispersion amount of the antiplatelet agent dispersed uniformly into the polymer or copolymer of the vinyl derivative. Within the range including the upper limit, the larger the amount, the greater the release rate of the antiplatelet agent. On the other hand, when the antiplatelet agent is contained in the large amount exceeding the above upper limit, the release rate is decreased after all. However, a duration time thereof is expected to be prolonged. Accordingly, it is desirable to select a suitable amount of the antiplatelet agent according to a kind, object or application use of the medical material to be produced.

The medical material of the present invention can be suitably used to, for example, a material for medical device. As an example of the medical device which can be produced by the material of the present invention, there are blood vessel catheter, cannula, monitoring tube, artificial kidney, pump-oxgenator, blood circuit for extracorporeal circulation, A-V shunt for artificial kidney, vascular prosthesis, artificial heart, artificial cardiac valve, temporary bypass tube of blood, blood line for hemodialysis, stent, blood bag, disposable circuit of blood cell separator, film or hollow fiber dialysis membrane and the like.

Hereinafter, the material of the present invention and a process for producing a device using the material of the present invention will be explained. Typical production process includes a solution method and a melting method. In the solution method, the polymer or copolymer of the vinyl derivative having the polar group and the antiplatelet agent are uniformly dissolved in a solvent and then the solvent is removed to give a medical material of the present invention. Examples of the solvent include dimethylformamide, dimethylacetamide, dimethyl sulfoxide, cyclohexanone, tetrahydrofuran, chloroform, dichloromethane, acetone and 1,1,1,3,3,3-hexafluoro-2-propanol, and a mixed solvent of two or more sorts of them. Among them, tetrahydrofuran is preferable to polyvinyl chloride, 1,1,1,3,3,3-hexafluoro-2-1-propanol or dimethyl sulfoxide is preferable to ethylene-vinyl alcohol copolymer, and methylene chloride or chloroform is preferable to poly(methyl methacrylate), because the solvent can be easily distilled off and has high solubility.

It is preferred that the polymer or copolymer of the vinyl derivative to be used is sufficiently washed by a method such as Soxhlet extraction in advance to remove impurities in the polymer or copolymer. Further, it is preferred that it is sufficiently dried to remove water in the polymer or copolymer.

The molding can be conducted by casting a solution wherein the above respective components are dissolved in a solvent on a glass plate, extruding into a tubular extrudate or applying on the other structure, followed by removing the solvent. Thereby, the polymer or copolymer of the vinyl derivative can be made into a film-like or tubular form, or coated. The solvent can be removed by air-drying, drying with heating under reduced pressure, phase transition due to a solidifying solution and the like. Examples of the coagulating solution include poor solvents of the polymer or copolymer, e.g. water, alcohols such as methanol, ethanol, propanol, butanol, etc., ketones such as acetone, etc. In this case, it is necessary to prevent the antiplatelet agent from dissolving in the coagulating solution during coagulation of the polymer material in every way. Accordingly, when solvency of the antiplatelet agent to the poor solvent of the polymer material is large, it is preferred to use a coagulating solution wherein a solvent for reducing the solvency of the antiplatelet agent is mixed with the poor solvent of the polymer material to solidify the polymer material and the antiplatelet agent contained therein, simultaneously.

A manner of molding a tubular device by the solution method will be explained in detail hereinafter. Firstly, a solution wherein the above respective components are dissolved in a solvent is applied on the surface of a suitable stem and then dried to form a tube, which is stripped from the stem. Otherwise, the above solution is applied on the surface of the stem, which is dipped in a coagulation solution to coagulate the polymer on the surface of the stem to give a tube and, thereafter, the resulting tube is stripped from the stem and is dried. The tubular device can also be produced by drying after the solution was extruded into a hollow form in the solidifying solution. Furthermore, the tubular device can also be produced by coating on a ready-made device such as vascular prosthesis, blood circuit, blood line for hemodialysis, etc. according to a dipping method, vacuum method, gas compression transmission method, rotary drum method and the like.

When molding a film-like material by the solution method, for example, there can be used a method of molding into a film such as a method comprising casting a solution on a glass plate and then drying to remove the solvent, a method comprising coating a solution directly on a woven fabric, knitted web, non-woven fabric, etc., or impregnating the solution into a woven fabric, knitted web, non-woven fabric, etc., and then drying to remove the solvent and the like. Further, the film-like material can also be produced by provided with a coating to produce a ready-made film according to a dipping method, spraying method and the like. The film thus obtained can be further coated to produce a multi-layer film.

In the solution method, the rate of the antiplatelet agent released from a molded article can be controlled by varying the amount of the antiplatelet agent contained in the polymer or copolymer, kind of the polymer or copolymer or method of removing the solvent (e.g. a method of drying under normal or reduced pressure, or a method of coagulating using a coagulation solution) and the like. Particularly, when using soft polyvinyl chloride as polyvinyl chloride, the release rate can also be controlled by the blending of plasticizers, stabilizers, secondary plasticizers, lubricants and the like. In case of coating, the release amount can be controlled more precisely by repeating coating plural times and varying conditions such as amount described above. Particularly, in case of coating on the ready-made device, it is preferred that, regarding a device staying in a living body for a long period of time, multi-layer coating is conducted to make the amount of the platelet agent of the inner layer large and to make that of the outer layer small. This enables sustained release of drug for a long period of time while maintaining physical properties of the material.

The solution methods described above are particularly effective when using the drug which is thermally unstable as the antiplatelet agent.

On the other hand, in case of the melting method, the polymer or copolymer of the vinyl derivative having the polar group is mixed with the antiplatelet agent in a molten state to obtain a medical material of the present invention. The melting must be conducted so that the antiplatelet agent is uniformly dispersed in the polymer or copolymer without causing decomposition of the antiplatelet agent. Therefore, a suitable antiplatelet agent and polymer or copolymer may be selected so that the polymer or copolymer is molten at a temperature lower than a decomposition temperature of the antiplatelet agent. Further, if necessary, oxidation of the antiplatelet agent or resin can be prevented if melting and molding operations are conducted in a non-oxygen atmosphere. It is preferred to remove water in the polymer or copolymer to be used as much as possible in view of stability of the drug and resin and accuracy of the molded article.

Various molding methods can be employed for the melting method, for example, a tubular or sheet-like molded article can be molded by an extrusion molding, and a molded article of a complicated structure can be molded by an injection molding. It is also possible to coat on a metal wire by using a crosshead.

The amount of the antiplatelet agent released from the molded article can also be controlled in melting molding by varying the amount of the antiplatelet agent in the polymer or copolymer, kind of the polymer or copolymer and the like. Particularly, when using polyvinyl chloride, it is possible to control release of the antiplatelet agent by the blending of additives such as plasticizers, stabilizers, secondary plasticizers, lubricants and the like, similar to the solution method. By conducting multi-layer (multi-color) molding and varying the amount or kind of the antiplatelet agent in the respective layers (parts), physical properties required for the medical material can be obtained and, at the same time, anticoagulant activity can be developed only at the desired part and the release amount can be controlled more precisely.

In the present invention, a particularly preferred combination is that of cilostazol as the antiplatelet agent and an ethylene-vinyl alcohol copolymer. Since cilostazol is superior in compatibility with the ethylene-vinyl alcohol copolymer, cilostazol can be uniformly dispersed. Also, cilostazol can be uniformly dispersed in soft polyvinyl chloride by adjusting the blending of additives.

The material molded into a tubular form of the present invention, particularly that in which the ethylene-vinyl alcohol copolymer is used can be suitably used as a blood circuit for extracorporeal circulation, catheter, bypass tube and the like. Examples thereof include a tube having a three-layer structure wherein an ethylene-α-olefin copolymer elastomer layer, a maleic acid-modified polyethylene layer and a cilostazol-containing ethylene-vinyl alcohol copolymer layer are laminated in order from the outer layer. On the other hand, those which are molded into a tubular form using soft polyvinyl chloride can be used as a blood circuit for extracorporeal circulation, or blood line for hemodialysis, in addition to a catheter or a bypass tube. Further, a multi-layer tube of which layers have different compositions can be easily produced by molding using a multi-layer die.

When the material molded into a tubular form of the present invention is used for a peripheral circulation circuit during cardiopulmonary bypass, not only anticoagulant action but angiectatic action is developed by using cilostazol or dipyridamole as the antiplatelet agent to be blended. Therefore, circulatory failure of distal tissue caused by controlled shock can be improved, and it is more advantageous.

The material molded into a film-like form of the present invention can be used as a material for a blood bag, etc. Among them, a multi-layer film wherein a material having large gas permeability such as ethylene-vinyl acetate copolymer or ethylene-$\alpha$-olefin copolymer is used is particularly preferable as a platelet storage bag.

The material molded into a filament by an extrusion molding or molded into a coil-like or zig-zag form by an injection molding of the present invention can be suitably used as it is or after knitting, as a vascular stent. In this case, when cilostazol is used as the antiplatelet agent, not only thrombogenesis at the surface of the stent but endothelial proliferation of blood vessel is inhibited, therefore it is particularly preferred to prevent reclosure of blood vessel. Further, it is possible to produce a vascular stent from a stainless steel or tantalum wire of which surface is coated with the material of the present invention, using a crosshead, thereby, those having the same effect as that described above can be obtained.

As described above, examples wherein the material of the present invention is used for the medical device itself were explained. As other examples, it is also possible to dispose the material of the present invention molded into any form in the medical device, as a member for developing antiplatelet action. For example, there can be used a method of encapsulating film-like or particulate small fragments of the material of the present invention in a ready-made platelet storage bag, a method of fixing small fragments of the material of the present invention at the upstream in an extracorporeal circulation circuit and the like.

As described above, regarding the material of the present invention, it is possible to control the release rate of the antiplatelet agent by varying the kind, amount or blending method of the antiplatelet agent, kind of polymer or copolymer, blending of the additive and the like. The release rate can also be controlled by varying the shape to be molded, particularly surface area.

FIELD OF THE INDUSTRIAL APPLICABILITY

As described above, the medical material of the present invention has such an effect that it has high anticoagulate activity and inhibition action of platelet loss due to activation of platelet because the antiplatelet agent can be continuously dissolved in the effective concentration. Further, the process for producing the medical material of the present invention has such an effect that said material can be easily produced.

EXAMPLES

The following Examples further illustrate the present invention in detail but are not to be construed to limit the scope thereof.

Example 1

190 mg of soft polyvinyl chloride [comprising 100 parts by weight of polyvinyl chloride having an average degree of polymerization of 1300, 50 parts by weight of di-2-ethylhexyl phthalate (hereinafter referred to as "DOP"), 5 parts by weight of epoxidized soybean oil, 2.2 parts by weight of a stabilizer (mixture of calcium stearate and zinc stearate) and 0.1 parts by weight of a lubricant] and 10 mg of cilostazol were dissolved in 5 ml of tetrahydrofuran and the resulting solution was casted on a glass plate, which was allowed to stand at 40° C. for 5 hours under reduced pressure (−760 mmHg) to distill off tetrahydrofuran to give a transparent film. The amount of cilostazol for the resulting film was 5% by weight.

Example 2

According to the same manner as that described in Example 1 except that the glass plate on which the solution was casted was dipped in water at room temperature to cause coagulation and, after washing with water repeatedly, it was dried at 50° C. for 10 hours under reduced pressure (−760 mmHg), instead of distilling off tetrahydrofuran, a white film was obtained. The amount of cilostazol for the resulting film was 5% by weight.

Example 3

According to the same manner as that described in Example 1 except for using polyvinyl chloride containing 10 parts by weight of DOP, a transparent film was obtained.

100 Mg of the respective film obtained in Examples 1, 2 and 3 was collected, respectively, and charged in 10 ml of a normal saline (pH 7.4) heated to 37° C. in advance, and then shaken by a thermostatic shaker at 37° C. After shaking for one hour, a sample was taken out and charged in 10 ml of the other normal saline (pH 7.4) heated to 37° C., and then shaken by a shaking apparatus at 37° C. for one hour. Thereafter, this operation was repeated for 8 hours to determine a variation with time in cilostazol concentration in a dissolution solution. The results are shown in FIG. 1.

As is apparent from FIG. 1, continuous dissolution of cilostazol in the concentration exceeding the effective concentration (1.1 μg/ml) is observed in all of films of Examples 1, 2 and 3 from the beginning of dissolution to 8 hours after that. Accordingly, it is found that the respective films of Example 1, 2 and 3 have high anticoagulant activity.

Further, there is a difference in removing method of solvent between Examples 1 and 2. Therefore, it is found that a difference in dissolution concentration of cilostazol observed is caused by the above difference, which results in difference in release properties.

Further, there is a difference in amount of plasticizer between Examples 1 and 3. Therefore, it is found that a difference in release properties is also caused by the above difference.

In case of soft polyvinyl chloride, it is anxious about dissolution of the plasticizer, however, no dissolution of the plasticizer was observed in all Examples. As a result, it was confirmed that selective dissolution (release) of cilostazol can be conducted.

A film was produced according to the same manner as that described in Example 1 except for changing the amount of cilostazol for the film of polyvinyl chloride to 10% by weight. As a result, the resulting film was cloudy. It is considered that this is because cilostazol is contained in the amount exceeding the amount which causes a saturated state. Regarding the resulting film, the dissolution amount of cilostazol was examined according to the same manner as that described above. As a result, dissolution in the concentration exceeding the effective concentration was observed from the beginning of dissolution to 8 hours after that, however, the dissolution concentration was low in comparison with that of Example 1 (5% by weight).

Further, when the amount of the plasticizer was increased, the resulting film became cloudy in the lower amount of cilostazol. In addition, when the resulting film is transparent and the amount of cilostazol is the same, the larger the amount of the plasticizer, the higher the dissolution concentration. Even if the polymerization degree of polyvinyl chloride to be used is varied, the amount of cilostazol which causes formation of the cloudy film is scarcely influenced.

Example 4

After 450 mg of an ethylene-vinyl alcohol copolymer (manufactured by the Nippon Synthetic Chemical Industry Co., Ltd.), ethylene content: 32 molar %) was molten with heating on a hot plate at 180° C., cilostazol was added thereto. Immediately after that, the melt was kneaded with stirring and the resulting mixture was pressed by a pressing machine to give a film having a thickness of about 100 µm. The amount of cilostazol for the resulting film was 10% by weight.

Example 5

According to the same manner as that described in Example 4 except for using 475 mg of an ethylene-vinyl alcohol copolymer and 25 mg of cilostazol, a film was obtained.

100 Mg of the respective film obtained in Examples 4 and 5 was collected, respectively, and then tested according to the same manner as that described in Examples 1, 2 and 3 to determine a variation with time in cilostazol concentration in a dissolution solution. The results are shown in FIG. 2.

Figure 2:
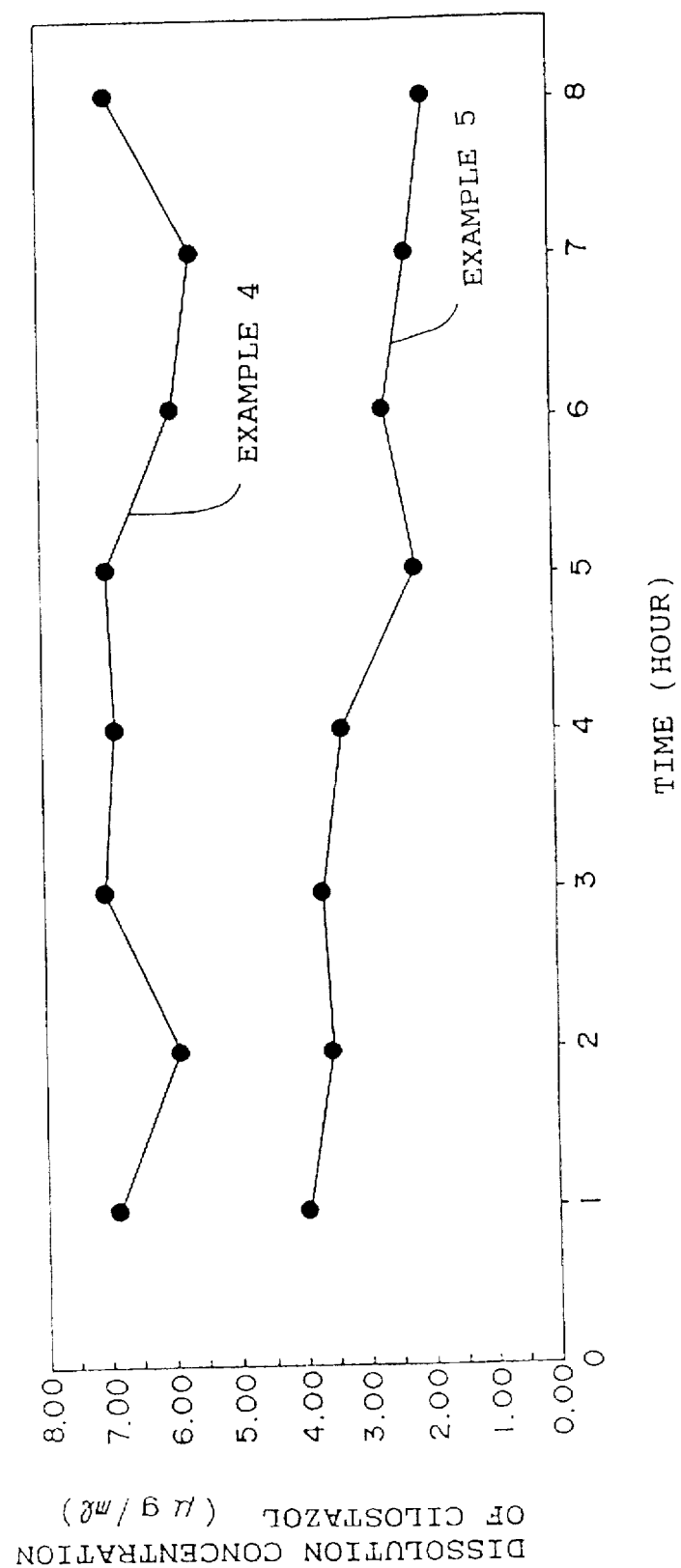
FIG. 2 is a graph illustrating a variation with time in dissolution concentration of drug obtained by using the respective films produced in Examples 4 and 5.

As is apparent from FIG. 2, gentle decrease of the dissolution amount is observed, however, sustained release of cilostazol in the concentration exceeding the effective concentration (1.1 µg/ml) until 8 hours after the beginning of dissolution is observed. Accordingly, it is found that the films of Examples 4 and 5 have high anticoagulant activity. Further, it is found that, the larger the amount of cilostazol (Example 4), the higher the dissolution concentration.

In Example 4, a transparent film could be obtained even if the amount of cilostazol was increased, until the amount reaches 20% by weight. However, when the amount exceeds 30% by weight, a cloudy film was obtained. Further, the dissolution amount of cilostazol was determined according to the same manner as that described above. As a result, dissolution of cilostazol in the amount exceeding the effective concentration was observed from the beginning to 8 hours after that in all films. However, regarding the cloudy film, the dissolution concentration exceeding that of the transparent film containing 20% by weight of cilostazol is not observed. Even if a kind of the ethylene-vinyl alcohol copolymer (e.g. ethylene content, molecular weight, saponification degree, etc.) was varied, the amount of cilostazol which causes formation of the cloudy film was scarcely influenced.

Example 6

(Production of blood bag)

To a film having a thickness of 250 µm, which is composed of soft polyvinyl chloride [comprising 100 parts by weight of polyvinyl chloride having an average degree of polymerization of 1100, 50 parts by weight of DOP, 5 parts by weight of epoxidized soybean oil, 0.3 parts by weight of a stabilizer (mixture of calcium stearate and zinc stearate) and 0.1 parts by weight of a lubricant], a solution of polyvinyl chloride (comprising 100 parts by weight of polyvinyl chloride having an average degree of polymerization of 1100 and 40 parts by weight of DOP) and cilostazol (contained in an amount of 5% by weight to a total solid content) in tetrahydrofuran (total concentration: 4% by weight) was continuously sprayed and dried to provide a coating on the surface of the film in a thickness of 10 µm. The resulting coated films were combined each other so that the coated surface becomes an inner surface, and then subjected to a high frequency heating adhesion to give a blood bag.

Example 7

(Production of vascular prosthesis)

After the inner/outer surfaces of a vascular prosthesis manufactured by Japan Gore-Tex Co., Ltd. (Gore-Tex EPTFE graft, straight graft, inner diameter: 3 mm, length: 10 cm) were subjected to a glow discharge treatment, the vascular prosthesis was dipped in ethanol to remove air bubble in a cavity under reduced pressure. Thereafter, the vascular prosthesis was coated with a solution of an ethylene-vinyl alcohol copolymer (manufactured by Nippon Synthetic Chemical Industry Co., Ltd., ethylene content: 32 molar %) and cilostazol (contained in an amount of 10% by weight to a total solid content) in 1,1,1,3,3,3-hexafluoro-2-propanol (total concentration: 5% by weight) while circulating the solution by an equipment shown in FIG. 3 to retain the porous structure, thereby to obtain a vascular prosthesis having an anticoagulate coating. The amount of coating to the vascular prosthesis was about 200 mg.

Figure 3:
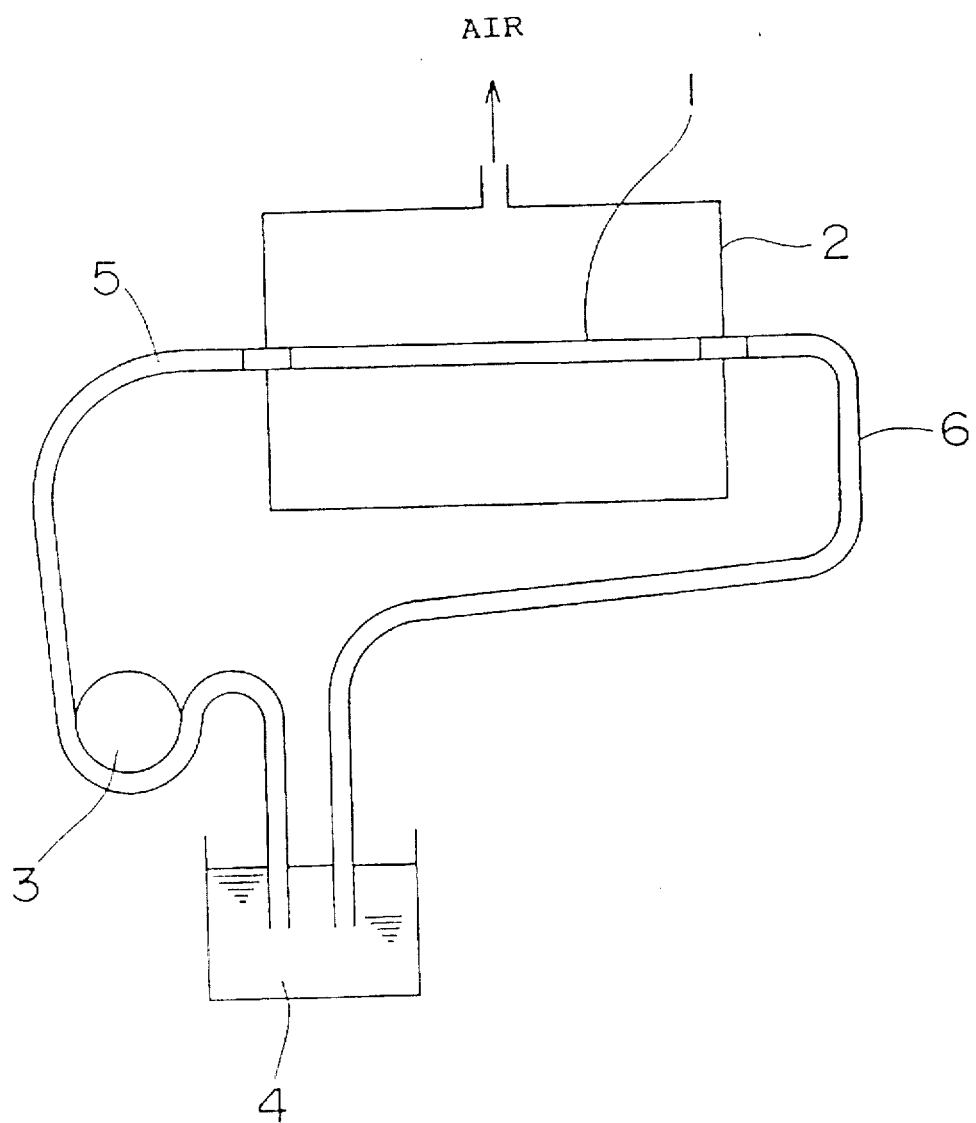
FIG. 3 is a schematic diagram illustrating the equipment used in Example 7.

In FIG. 3, a vascular prosthesis 1 is contained in a vacuum chamber 2. To both ends of the vascular prosthesis 1, pipes 5 and 6 for circulation are connected, respectively. The solution 4 of the ethylene-vinyl alcohol copolymer and cilostazol is circulated in the vascular prosthesis 1 using a pump 3 to coat the blood vessel.

Example 8

(Production of blood line for hemodialysis)

The inner surface of a main tube of a blood circuit (CLIRANS Blood Line for hemodialysis) manufactured by Terumo Corporation, was coated with a solution of polyvinyl chloride (comprising 100 parts by weight of polyvinyl chloride having an average degree of polymerization of 1100 and 40 parts by weight of DOP) and cilostazol (contained in an amount of 5% by weight to a total solid content) in tetrahydrofuran (total concentration: 10% by weight) by a rotating drum method to produce a blood circuit having an anticoagulant coating of 10 µm in thickness.

Example 9

(Production of blood circuit)

Soft polyvinyl chloride [comprising 100 parts by weight of polyvinyl chloride having an average degree of polymerization of 800, 40 parts by weight of DOP, 7 parts by weight of epoxidized soybean oil, 3 parts by weight of a stabilizer (mixture of calcium stearate and zinc stearate) and 0.2 parts by weight of a lubricant] was mixed with cilostazol in the melting condition at a proportion of 5% by weight of cilostazol to the total amount. By using the above soft polyvinyl chloride containing cilostazol and soft polyvinyl chloride [comprising 100 parts by weight of polyvinyl chloride having an average degree of polymerization of 1700, 70 parts by weight of DOP, 6 parts by weight of epoxidized soybean oil, 2.2 parts by weight of a stabilizer (mixture of calcium stearate and zinc stearate) and 0.1 parts by weight of a lubricant], a two-layer tube having an outer diameter of 7 mm, an inner diameter of 4.5 mm and a thickness of 1.25 mm was produced by a co-extrusion molder equipped with a circular die under a nitrogen atmosphere. The resulting tube was composed of a soft polyvinyl chloride layer(thickness: 1.00 mm) as an outer layer and a cilostazol-containing soft polyvinyl chloride layer (thickness: 0.25 mm) as an inner layer.

Example 10

360 Mg of an ethylene-vinyl alcohol copolymer (ethylene content: 32 molar %, manufactured by Nippon Synthetic Chemical Industry Co., Ltd.) and 40 mg of cilostazol were dissolved in 10 ml of 1,1,1,3,3,3-hexafluoro-2-propanol and the resulting solution was casted on a glass plate, which was dried at room temperature for 8 hour and further dried by a vacuum drier at 40° C. for 24 hours to give a transparent film (thickness: about 50 μm). The amount of cilostazol of the resulting film was 10% by weight.

100 Mg of the resulting film was collected and then tested according to the same manner as that described in Example 1, 2 and 3. As a result, continuous release of cilostazol in the concentration exceeding the effective concentration was observed, similar to those obtained in Examples 4 and 5.

In this production process, a cloudy film was obtained when the amount of cilostazol exceeds 20% by weight.

Example 11

360 Mg of poly(methyl methacrylate) (manufactured by Sumitomo Chemical Company, Ltd.) and 40 mg of cilostazol were dissolved in 10 ml of chloroform and the resulting solution was casted on a glass plate, which was dried at room temperature for 8 hours and further dried by a vacuum drier at 40° C. for 24 hours to give a transparent film (thickness: about 50μ).

100 Mg of the resulting film was collected and then tested according to the same manner as that described in Example 1, 2 and 3. As a result, continuous release in the concentration exceeding the effective concentration was observed.

Example 12

360 Mg of an ethylene-vinyl alcohol copolymer (manufactured by Nippon Synthetic Chemical Industry Co., Ltd., ethylene content: 32 molar %) and 40 mg of dipyridamole were dissolved in 10 ml of 1,1,1,3,3,3-hexafluoro-2-propanol and the resulting solution was casted on a glass plate, which was dried at room temperature for 8 hours and further dried by a vacuum drier at 40° C. for 24 hours to give a transparent film (thickness: about 50μ).

In this production process, a cloudy film was obtained when the amount of dipyridamole exceeds 20% by weight.

Example 13

An ethylene-vinyl alcohol copolymer (manufactured by Nippon Synthetic Chemical Industry Co., Ltd, ethylene content: 44 molar %) was pulverized by a chemical mill (model R-8) to collect particles having a particle size of 50 to 125 μm. 900 Mg of the resulting particles were mixed with 100 mg of dipyridamole and the mixture was pressed by a compact type test press (manufactured by Toyo Seiki Co., Ltd.) at 180° C. for 2 minutes to give a transparent film having a thickness of about 100 μm.

In this production process, an opaque film was obtained when the amount of dipyridamole exceeds 20% by weight.

Figure 4:
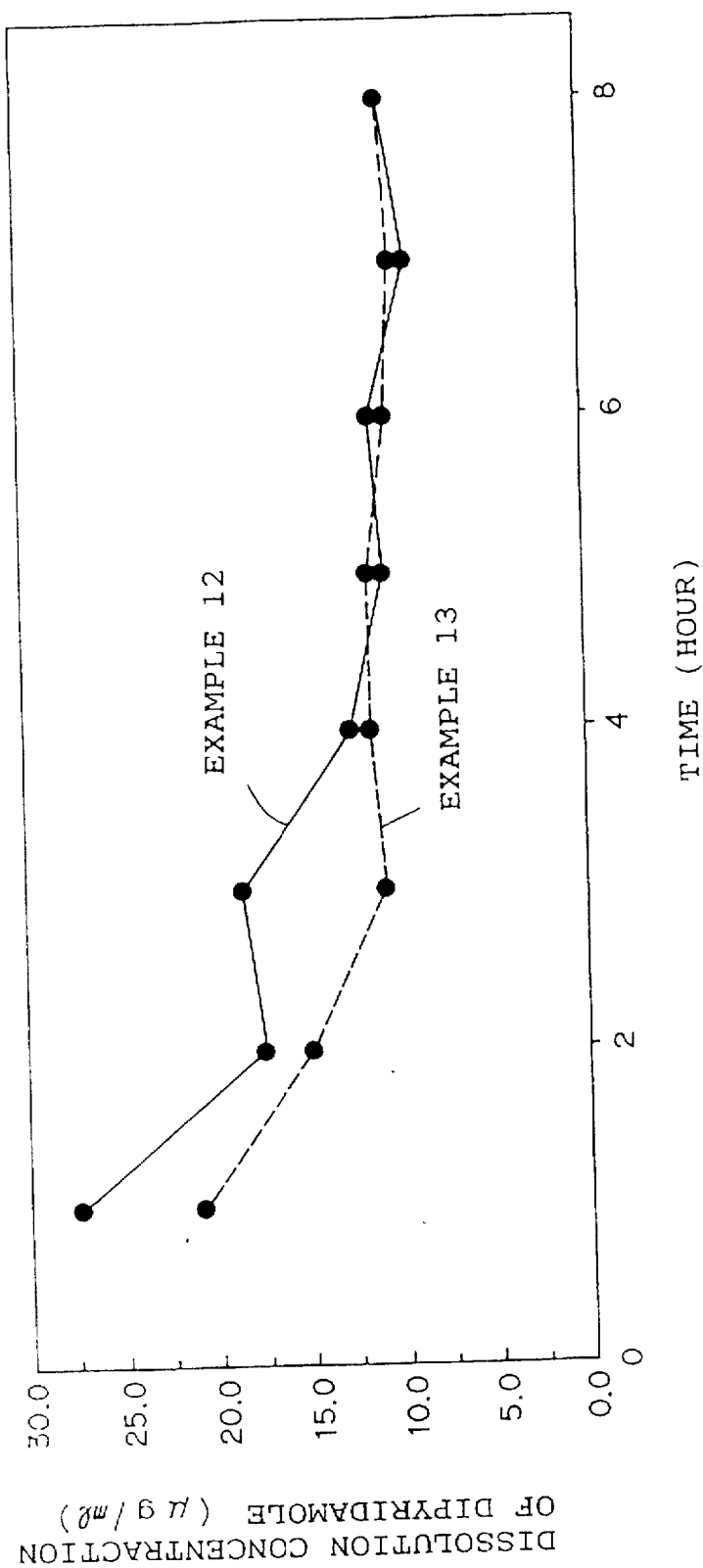
FIG. 4 is a graph illustrating a variation with time in dissolution concentration of drug obtained by using the respective films produced in Examples 12 and 13.

100 Mg of the respective film obtained in Examples 12 and 13 was collected, respectively, and then tested according to the same manner as that described in Example 1, 2 and 3. As a result, continuous release of dipyridamole in the concentration exceeding the effective concentration (1.8 μg/ml) was observed until 8 hours after the beginning of dissolution (see FIG. 4).

Example 14

173 Mg of polyvinyl chloride (manufactured by Shin-Etsu Chemical Co., Ltd., KP-13 E), 17 mg of DOP and 10 mg of dipyridamole were dissolved in 5 ml of tetrahydrofuran and the resulting solution was flowed and applied on a glass plate, which was dried by a vacuum drier at 40° C. for 24 hours to give a transparent film (thickness: about 50μ).

Example 15

Poly(methyl methacrylate) (manufactured by Sumitomo Chemical Company Ltd.) was pulverized by a chemical mill(model R-8) to collect particles having a particle size of 50 to 125 μm. 950 Mg of the resulting particles were mixed with 50 mg of dipyridamole and the mixture was pressed by a compact type test press (manufactured by Toyo Seiki Co., Ltd.) at 180° C. for 2 minutes to give a transparent film having a thickness of about 100 μm.

Regarding a relation between a kind of the resin and a dispersed state of the drug as well as a relation between the kind of the resin and release properties of the drug, cilostazol and dipyridamole showed same tendency.

Example 16

360 Mg of an ethylene-vinyl alcohol copolymer (manufactured by Nippon Synthetic Industry Co., Ltd., ethylene content: 32 molar %) and 40 mg of aspirin were dissolved in 10 ml of 1,1,1,3,3,3-hexafluoro-2-propanol and the resulting solution was flowed and applied on a glass plate, which was dried at room temperature for 8 hours and further dried by a vacuum drier at 40° C. for 24 hours to give a transparent film (thickness: about 50μ).

In this production process, a cloudy film was obtained when the amount of aspirin exceeds 20% by weight.

Example 17

127 Mg of polyvinyl chloride (manufactured by Shin-Etsu Chemical Co., Ltd., KP-13 E), 63 mg of DOP and 10 mg of aspirin were dissolved in 5 ml of tetrahydrofuran and the resulting solution was casted on a glass plate, which was dried by a vacuum drier at 40° C. for 24 hours to give a transparent film (thickness: about 50μ).

Example 18

360 Mg of poly(methyl methacrylate) (manufactured by Sumitomo Chemical Company Ltd.) and 40 mg of aspirin were dissolved in 10 ml of chloroform and the resulting solution was casted on a glass plate, which was dried at room temperature for 8 hours and further dried by a vacuum drier at 40° C. for 24 hours to give a transparent film having a thickness of about 50 μm.

Regarding a relation between a kind of the resin and a dispersed state of the drug as well as a relation between the kind of the resin and release properties of the drug, aspirin and cilostazol showed same tendency.

Figure 5:
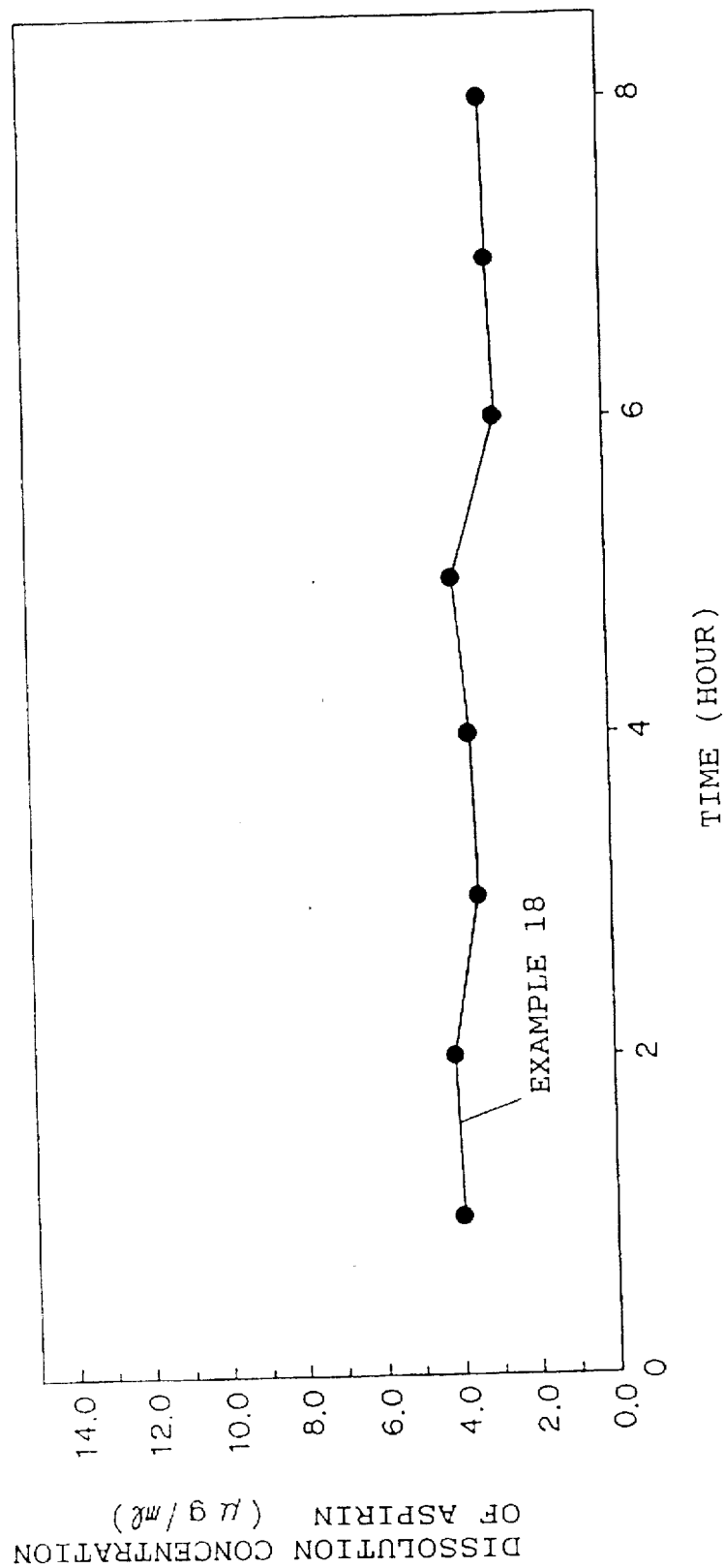
FIG. 5 is a graph illustrating a variation with time in dissolution concentration of drug obtained by using the film produced in Example 18.

100 Mg of the film obtained in Example 18 was collected and then tested according to the same manner as that described in Example 1, 2 and 3. As a result, continuous release of aspirin in the concentration exceeding the effective concentration (1 μg/ml) was observed until 8 hours after the beginning of dissolution (see FIG. 5)

Example 19

(Production of vascular stent)

500 Mg of a Palmaz-Shatz stent (manufactured by Johnson & Johnson Co., U.S.A.) was dipped in an ethylene-vinyl alcohol copolymer-cilostazol solution [prepared by dissolving 500 mg of an ethylene-vinyl alcohol copolymer (manufactured by Nippon Synthetic Chemical Industry Co., Ltd., Soarnol K3825N) and 500 mg of cilostazol in 100 ml of hexafluoro-2-propanol, amount of cilostazol: 50% by weight] and, after air-drying, the stent was dipped and air-dried again. This operation was repeated to produce a coating layer (amount of cilostazol: 50 % by weight) having a thickness of about 50 μm. The resulting coated stent was dried at 40° C. for 72 hours under vacuum to remove the solvent completely. Thereafter, it was dipped in an ethylene-vinyl alcohol copolymer-cilostazol solution [newly prepared by dissolving 950 mg of an ethylene-vinyl alcohol copolymer (manufactured by Nippon Synthetic Chemical Industry Co., Ltd., Soarnol K3825N) and 50 mg of cilostazol in 100 ml of 1,1,1,3,3,3-hexafluoro-2-propanol] and then air-dried. This operation was repeated to produce a second coating layer (amount of cilostazol: 5% by weight) on the above coating layer.

Example 20

(Production of stent)

An ethylene-vinyl alcohol copolymer (manufactured by Kuraray Co., Ltd., ethylene content: 44 molar %) was pulverized by a pulverizer (manufactured by Fritsch Co., rotor speed mill) to collect particles having a particle size of 50 to 125 μm. Then, 45 g of the particles were dryblended with 5 g of cilostazol (manufactured by Otsuka Pharmaceutical Co., Ltd.) and the mixture was extruded with kneading at 180° C. under a nitrogen atmosphere by an extruder (manufactured by CSI Co., CS-194A MAX MIXING EXTRUDER). Thereafter, the extrudate was stretched to produce an ethylene-vinyl alcohol copolymer filament having a size of 0.25 μm in diameter, wherein cilostazol is uniformly dispersed. The amount of cilostazol in the resulting copolymer filament was 10% by weight.

16 Filaments were interwound to produce a self-expanding type stent (wall type stent) having a length of 2 cm, an outer diameter on expansion of 2.5 mm and an outer diameter on shrinkage of 1.4 mm.

Example 21

(Production of catheter)

1.8 G of poly(methyl methacrylate) (manufactured by Sumitomo Chemical Company Ltd.) and 0.2 g of cilostazol (manufactured by Otsuka Pharmaceutical Co., Ltd.) were dissolved in 100 ml of chloroform. The resulting solution was coated on the inner and outer surfaces of a single lumen catheter having an inner diameter of 1.2 mm, an outer diameter of 2.0 mm and a length of 70 cm, which was prepared in advance by molding soft polyvinyl chloride, in the coating thickness of about 100 μm.

Example 22

(Production of blood circuit connector)

Figure 6A:
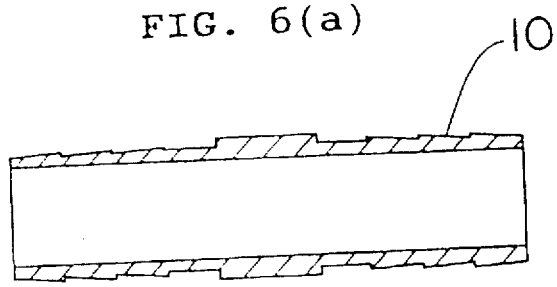
FIGS. 6 (a), (b) and (c) are respectively sectional, side and elevational views illustrating the blood circuit connector for pump-oxgenator produced in Example 22.
Figure 6B:
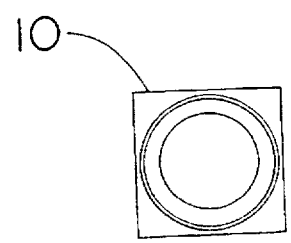
Figure 6C:
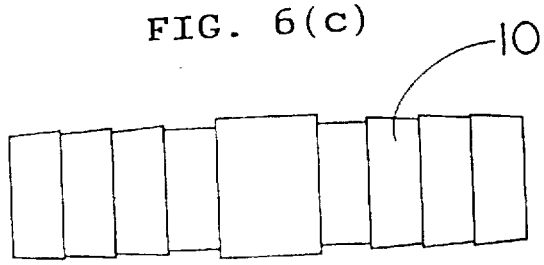

Poly(methyl methacrylate) (manufactured by Sumitomo Chemical Company Ltd.) was pulverized by a pulverizer (manufactured by Fritsch Co., rotor speed mill) and screened to collect particles having a particle size of 50 to 125 μm. Then, 95 g of the particles were dryblended with 5 g of cilostazol and the blend was extruded with kneading at 180° C. under a nitrogen atmosphere by an extruder (manufactured by CSI Co., CS-194A MAX MIXING EXTRUDER) using a strand die. After the extrudate was pelletized, a blood circuit connector 10 for pump-oxgenator having the shape shown in FIG. 6 was produced by an injection molding using a midget molder.

We claim:

1. A medical material comprising a polymer or copolymer of a vinyl derivative having a polar group as a part thereof, wherein said material uniformly contains therein an antiplatelet agent selected from the group consisting of cilostazol, dipyridamole and satigrel.

2. The medical material according to claim 1, wherein the polar group is a hydroxyl group, a chlorine atom, a cyano group or an alkoxycarbonyl group.

3. The medical material according to claim 1, wherein the polar group is a hydroxyl group, a chlorine atom or an alkoxycarbonyl group.

4. The medical material according to claim 1, wherein the polar group is a hydroxyl group, a lower alkoxycarbonyl group or a chlorine atom.

5. The medical material according to claim 1, wherein the polymer or copolymer is polyvinyl chloride, ethylene-vinyl alcohol copolymer, polyacrylonitrile, polymethacrylate or polyacrylate.

6. The medical material according to claim 1, wherein the polymer or copolymer is polyvinyl chloride, polymethacrylate or ethylene-vinyl alcohol copolymer.

7. The medical material according to claim 1, wherein the polymer or copolymer is an ethylene-vinyl alcohol copolymer.

8. The medical material according to claim 1, wherein the amount of the antiplatelet agent is 0.01 to 60 parts by weight based on 100 parts by weight of the medical material.

9. The medical material according to claim 8, wherein the amount of the antiplatelet agent is 1 to 44.4 parts by weight based on 100 parts by weight of the medical material.

10. The medical material according to claim 9, wherein the amount of the antiplatelet agent is 4.8 to 33.3 parts by weight based on 100 parts by weight of medical material.

11. The medical material according to claim 1, wherein the amount of the antiplatelet agent is not more than 20% by weight based on the total weight.

12. The medical material according to claim 1, wherein the antiplatelet agent is at least one selected from the group consisting of cilostazol, dipyridamole, and satigrel.

13. A medical material comprising a polymer or copolymer of a vinyl derivative having a polar group as a part thereof, wherein said material uniformly contains therein cilostazol.

14. The medical material according to claim 13, wherein the amount of cilostazol is 0.01 to 60 parts by weight based on 100 parts by weight of the medical material.

15. The medical material according to claim 14, wherein the amount of cilostazol is 1 to 44.4 parts by weight based on 100 parts by weight of the medical material.

16. The medical material according to claim 15, wherein the amount of cilostazol is 4.8 to 33.3 parts by weight based on 100 parts by weight of the medical material.

17. The medical material according to claim 13, wherein the amount of cilostazol is not more than 20% by weight based on the total weight.

18. The medical material according to claim 13, 14, 15, 16 or 17, wherein the polymer or copolymer is polyvinyl chloride, ethylene-vinyl alcohol copolymer, polyacrylonitrile, polymethacrylate or polyacrylate.

19. The medical material according to claim 18, wherein the polymer or copolymer is an ethylene-vinyl alcohol copolymer.

20. The medical material according to claim 19, wherein the material contains therein cilostazol.

21. The medical material according to claim 20, wherein the amount of cilostazol is not more than 20% by weight based on the total weight of the material.

22. A medical material wherein a polymer or copolymer of a vinyl derivative having a polar group as part thereof and cilostazol are mixed in a molten state.

23. The medical material according to claim 22, wherein the polymer or copolymer is an ethylene-vinyl alcohol copolymer.

24. A process for producing a medical material which comprises mixing a polymer or copolymer of a vinyl derivative having a polar group as a part thereof with an antiplatelet agent selected from the group consisting of cilostazol, dipyridamole and satigrel in a molten state.

25. A process for producing a medical material which comprises dissolving a polymer or copolymer of a vinyl derivative having a polar group as a part thereof and an antiplatelet agent selected from the group consisting of cilostazol, dipyridamole and satigrel in a solvent and then removing the solvent.

26. The medical material according to claim 1 to 13, 20 or 21, wherein the medical material is a material for medical device.

27. A process for producing the medical material of claim 24 or 25, wherein the medical material is a material for medical device.

28. A process for producing the medical material of claim 24 or 25, wherein the antiplatelet agent is cilostazol.

29. The process for producing a medical material according to claim 27, wherein the antiplatelet agent is cilostazol.

30. The process of claim 24 wherein said polymer or copolymer is selected from the group consisting of polyvinyl chloride, ethylene-vinyl alcohol copolymer, polyacrylonitrile, polymethylacylate or polyacylate.

31. The process of claim 25 wherein said polymer or copolymer is selected from the group consisting of polyvinyl chloride, ethylene-vinyl alcohol copolymer, polyacrylonitrile, polymethylacylate or polyacylate.

* * * * *